United States Patent [19]

Yoshioka et al.

[11] 4,101,658

[45] Jul. 18, 1978

[54] ANTIBACTERIAL HYDRAZONO CEPHALOSPORINS

[75] Inventors: Mitsuru Yoshioka, Toyonaka; Yuji Sendo, Nishinomiya; Koji Ishikura, Amagasaki; Masayuki Murakami, Itami; Sadao Miyazaki, Toyonaka, all of Japan

[73] Assignee: Shionogi & Co., Ltd., Osaka, Japan

[21] Appl. No.: 583,696

[22] Filed: Jun. 4, 1975

[51] Int. Cl.² .................. A61K 31/545; C07D 501/20
[52] U.S. Cl. ..................... 424/246; 542/416; 542/417; 542/418; 542/424; 544/16; 544/21
[58] Field of Search ............. 260/243 C; 424/246; 544/16, 21; 542/416, 417, 418, 424

[56] References Cited

U.S. PATENT DOCUMENTS

| | | | |
|---|---|---|---|
| 3,351,596 | 11/1967 | Chamberlin | 260/243 C |
| 3,769,277 | 10/1973 | Long et al. | 260/243 C |
| 3,799,922 | 3/1974 | Jen et al. | 260/243 C |
| 3,987,039 | 10/1976 | Yoshioka et al. | 544/16 |
| 3,997,528 | 12/1976 | Yoshioka et al. | 260/243 C |

*Primary Examiner*—Nicholas S. Rizzo
*Attorney, Agent, or Firm*—Birch, Stewart, Kolasch and Birch

[57] ABSTRACT

Antibacterial cephalosporins of the following formula:

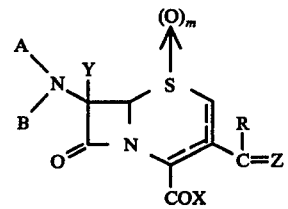

wherein A and B each is a hydrogen or an amino protecting group; X is a hydroxy or a carboxy protecting group; Y is a hydrogen, halogen, alkyl, alkoxy, or an alkylthio; R is a hydrogen or an alkyl; Z is a group of the formula

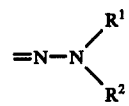

(in which $R^1$ and $R^2$ are the same or different and are a hydrogen, optionally substituted hydrocarbon group, organic acyl, or a group of the formula

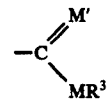

respectively, in which M and M' are the same or different and are an oxygen or sulfur; $R^3$ is a hydrocarbon group; $R^1$ and $R^2$ can be combined together directly or through a hetero atom); m is 0 or 1; and the broken line shows the presence of a double bond at position 2 or 3, preparable from the compounds shown by the above formula in which Z is an oxygen by treatment with a compound shown by the formula $H_2Z$; and pharmaceuticals containing these compounds.

7 Claims, No Drawings

ANTIBACTERIAL HYDRAZONO CEPHALOSPORINS

This invention relates to a cephalosporin compound of the following formula:

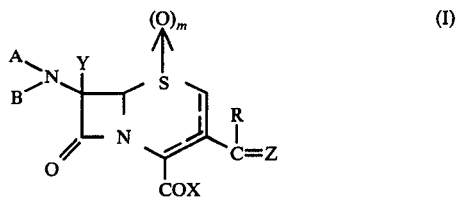

wherein A and B each is a hydrogen or an amino protecting group; X is a hydroxy or a carboxy protectiong group; Y is a hydrogen, halogen, alkyl, alkoxy, or an alkylthio; R is a hydrogen or an alkyl; Z is a group of the formula

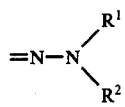

(in which $R^1$ and $R^2$ are the same or different and are a hydrogen, optionally substituted hydrocarbon group, organic acyl, or a group of the formula

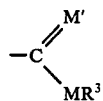

respectively, in which M and M' are the same or different and are an oxygen or sulfur; $R^3$ is a hydrocarbon group; $R^1$ and $R^2$ can be combined together directly or through a hetero atom); m is 0 or 1; and the broken line shows the presence of a double bond at position 2 or 3.

In the above formula (I), the amino protecting group represented by A or B can be an acyl, silyl, sulfinyl, hydrocarbyl or other amino protecting groups containing 1 to 20 carbon atoms which include the corresponding groups in the side chain of natural or synthetic penicillins or cephalosporins.

The acyl group represented by A or B in the above formula (I) includes such an inorganic acyl as carbonic acyl (e.g. alkoxycarbonyl, haloalkoxycarbonyl, aralkoxycarbonyl, aryloxycarbonyl), sulfuric acyl, phosphoric acyl (e.g. dialkoxy phosphonyl, dialkoxythiophosphonyl, alkoxyaminophosphonyl), and other inorganic acyl groups; and such organic acyl groups as alkanoyl, cycloalkanoyl, aralkanoyl, aroyl, alkylsulfonyl, arylsulfonyl, alkylphosphonyl, or other organic acyls. These acyl groups can, where possible, be unsaturated or substituted by a halogen (e.g. fluorine, chlorine, bromine), nitrogen function (e.g. amino, hydrazino, azido, alkylamino, arylamino, acylamino, alkylideneamino, acylimino, imino, nitro), oxygen function (e.g. hydroxy, alkoxy, aralkoxy, aryloxy, acyloxy, oxo), sulfur function (e.g. mercapto, alkylthio, aralkylthio, arylthio, acylthio, thioxo, sulfo, sulfonyl, sulfinyl, alkoxysulfonyl, aryloxysulfinyl), carbon function (e.g. alkyl, alkenyl, aralkyl, aryl, carboxy, carbalkoxy, carbamoyl, alkanoyl, aroyl, aralkanoyl, cyano), or a phosphorous function (e.g. phospho, phosphoro). A and B can be combined together forming a diacyl group of a polybasic acid (e.g. phthalyl, pyridine-2,3-dicarbonyl, maleoyl, succinyl).

The hydrocarbon group represented by A or B can be an easily removable aliphatic hydrocarbon group containing 1 to 20 carbon atoms (e.g. alkyl, alkenyl, aralkyl, or other aliphatic hydrocarbon groups optionally interrupted by a heteroatom in its main nucleus) or an easily removable mono-cyclic aromatic hydrocarbon group (e.g. phenyl, pyrimidyl); each can, where possible, be unsaturated or substituted by a substituent (e.g. halogen, nitrogen, oxygen, sulfur, carbon, or phosphorous functions or other substituents). A and B can be combined together forming a divalent hydrocarbon group (e.g. alkylene, aralkylene, alkylidene, aralkylidene, diarylmethylidene, cycloalkylidene) or other divalent hydrocarbon group which can be interrupted by a hetero atom in its main nucleus, or where possible be substituted by a substituent as shown above, or unsaturation. The group A being an acyl and the group B being a hydrocarbon group can be combined together with the nitrogen bound to position 7 of the cephem ring forming a cyclic group (e.g. 4-oxo-3-imidazolidinyl ring).

The silyl (e.g. trialkylsilyl) and sulfenyl (e.g. phenylsulfenyl, o-nitrophenylsulfenyl) represented by A or B are conventional amino protecting groups.

Antibacterially preferable acyl groups for A or B are:
(1) alkanoyl containing 1 to 3 carbon atoms,
(2) haloalkanoyl containing 2 to 3 carbon atoms,
(3) azidoacetyl,
(4) cyanoacetyl,
(5) acyl groups of the following formula:

$$Ar-CQ_2-CO-$$

in which Q is a hydrogen or methyl; and Ar is a thienyl, furyl, pyrrolyl, pyridyl, phenyl, or phenyl substituted by chlorine, bromine, iodine, fluorine trifluoromethyl, hydroxy, alkyl containing 1 to 3 carbon atoms, alkoxy containing 1 to 3 carbon atoms, cyano, or nitro, (6) acyl groups of the following formula:

$$Ar-G-CH_2-CO-$$

wherein G is an oxygen or sulfur; Ar is as defined above, (7) acyl groups of the following formula:

$$Ar-CHT-CO-$$

wherein Ar is as defined above; and T is (i) amino, ammonium, amino protected by benzyloxycarbonyl, alkoxycarbonyl containing 1 to 4 carbon atoms, cyclopentyloxycarbonyl, cyclohexyloxycarbonyl, benzhydryloxycarbonyl, triphenylmethyl, 2,2,2-trichloroethoxycarbonyl, guanidylcarbamoyl, sulfo, or amino protected in the forms of phthalimido, or enamines derived from acetoacetate or acetylacetone, (ii) hydroxy or alkanoyloxy containing 1 to 6 carbon atoms, (iii) carboxy or alkoxycarbonyl containing 2 to 7 carbon atoms, or (iv) azido, cyano, carbamoyl, or sulfo, (8) 2-sydnon-3-alkanoyl containing 3 to 5 carbon atoms, (9) (tetrazol-1-yl)alkanoyl containing 1 to 4 carbon atoms,

(10) 5-aminoadipoyl, 5-aminoadipoyl protected by alkanoyl containing 1 to 3 carbon atoms, or chloroalkanoyl containing 1 to 3 carbon atoms at the amino group; or 5-aminoadipoyl protected by benzhydryl, 2,2,2-trichloroethyl, alkyl containing 1 to 6 carbon atoms, nitrobenzyl or methoxybenzyl at the carboxy group; and

(11) a diacyl group derived from a polybasic carboxylic acid containing 4 to 12 carbon atoms.

The carboxy protecting group containing up to 20 carbon atoms represented by X can be such oxygen functions as alkoxy containing 1 to 8 carbon atoms (e.g. methoxy, trichloroethoxy), aralkoxy containing 7 to 20 carbon atoms (e.g. benzyloxy, methoxybenzyloxy, nitrobenzyloxy, diphenylmethoxy, trityloxy), mono- or bicyclic aryloxy (e.g. phenoxy, naphthyloxy), organometaloxy (e.g. trimethylstannic oxy, trimethylsilyloxy), organic or inorganic acyloxy containing 1 to 8 carbon atoms, metaloxy of groups I, II, or III in the Periodic Table (e.g. sodiooxy, potassiooxy, mgnesiodioxy, aluminumtrioxy), and other oxygen functions; sulfur functions such as these forming thiol ester, thiocarboxy, or like groups; nitrogen functions such as those forming amide, hydrazide, azide, or like groups; and other groups. These groups can, where possible be unsaturated or substituted by a substituent given above (e.g. nitrogen, oxygen, sulfur, carbon, or phsophorous functions or halogens as shown above). Among the carboxy protecting groups, these which can be removed without adverse effect on the other part of the molecule are preferable. Preferable groups are, for example, these which form haloalkyl ester containing 1 to 3 carbon atoms, acylalkyl ester containing 2 to 10 carbon atoms, alkoxyalkyl ester containing 2 to 8 carbon atoms, acyloxyalkyl ester containing 2 to 8 carbon atoms, carbalkoxyalkyl ester containing 3 to 8 carbon atoms, phenyl ester, aralkyl ester containing 7 to 20 carbon atoms, ester with an oxime containing 2 to 10 carbon atoms, N-alkoxyamide containing 1 to 5 carbon atoms, imide with saccharin, imide with phthalimide, N,N'-diisobutylhydrazide, metal salts, alkylamine salts containing 1 to 6 carbon atoms, or the groups equivalent in effect to these groups (In the definition given above, specified numbers of carbon atoms are for groups X). Antibacterially preferable carboxy protecting groups X include those which form acyloxymethyl esters, phenacyl esters, benzaldoxime ester, N,N-dimethylaminoethyl ester, alkali metal salts, alkaline earth metal salts, and other groups equivalent in effect to these groups.

Y can be a hydrogen, alkoxy containing 1 to 3 carbon atoms (e.g. methoxy, ethoxy, hydroxymethoxy), alkylthio containing 1 to 3 carbon atoms (e.g. methylthio, ethylthio), alkyl containing 1 to 3 carbon atoms (e.g. methyl, ethyl), or halogen (e.g. fluorine, chlorine, bromine), among which hydrogen and methoxy are preferable.

The compounds (I) where m is 0 are strong antibacterials, while those where m is 1 are useful intermediates for stabilization of the double bond at position 3.

The alkyl represented by R can be methyl, ethyl, propyl, isopropyl, cyclopropyl, or other straight, branched, or cyclic alkyl containing 1 to 3 carbon atoms. Hydrogen is the most preferably for R from the view point of antibacterial activity.

Among the double bonds represented by the broken line, those at position 3 are preferable for antibacterial activity, while those at position 2 are useful as intermediates for preparing the compounds (I) with a double bond at position 3.

It is apparent that syn- and anti- isomers can be formed around the carbon nitrogen double bond in the substituent at position 3 of the cephem nucleus. The ratio of formed isomers depends on the reaction and starting materials. In this application, both isomers are represented by or included in the same structural formula or nomenclature.

The preferable group Z includes the following groups:

(1) hydrazono;

(2) 2-(o- or p-carboxyphenyl)hydrazono, 2-(p-alkylsulfonylphenyl)hydrazono in which the said alkyl contains 1 to 3 carbon atoms, 2-(p-sulfophenyl)hydrazono which can form a salt with an alkali metal ion;

(3) 2-phenyl-2-alkylhydrazono in which the alkyl contains 1 to 3 carbon atoms;

(4) 2-(2-pyridyl)hydrazono, 2(thiazol-2-yl)hydrazono, 2-(1-amino-5-mercapto-1,3,5-triazol-2-yl)hydrazono, 2-(purin-6-yl)-hydrazono, 2-(4-oxoimidazolin-2-yl)hydrazono;

(5) 2-(sulfolan-3-yl)hydrazono, 2-(carbalkoxymethyl)hydrazono in which the carbalkoxy contains 2 to 5 carbon atoms;

(6) (pyrazin-1-yl)imino, (2-pyridon-1-yl)imino;

(7) 2-(alkanoyl)hydrazono in which the alkanoyl contains 1 to 4 carbon atoms, 2-glycylhydrazono, 2-(N-tertiary butoxycarbonylglycyl)hydrazono, 2-(trimethylammoniumacetyl)hydrazono, 2-(pyridiniumacetyl)hydrazono, 2-oxalylhydrazono, 2-(alkoxyalyl)hydrazono in which the alkoxyalyl contains 3 to 6 carbon atoms, 2-(amidoxalyl)-hydrozono, 2-(hydrazinodicarbonyl)hydrazono, 2-(cyanoacetyl)-hydrazono, 2-(gluconoyl)hydrazono, 2-(benzoyl)hydrazono, 2-(furoyl)hydrazono, 2-(isoxazol-3-yl)carbonylhydrazono, 2-(5-methylisoxazol-3-yl)carbonylhydrazono, 2-(1,2,5-thiadiazol-3-yl)carbonylhydrazono, 2-(5-methyl-1,2,3-thiadiazol-4-yl)carbonylhydrazono;

(8) 2-(carbalkoxy)hydrazono in which the carbalkoxy contains 2 to 5 carbon atoms, 2-(dithiocarbalkoxy)-hydrazono in which the dithiocarbalkoxy contains 2 to 5 carbon atoms; and other equivalent groups.

These compounds can be prepared by the following reactions:

(1) The reaction of an oxo compound (II) or its reactive derivatives and a hydrazine compound (III) or its reactive derivatives gives the cephalosporin compound (I), as is shown in the following scheme:

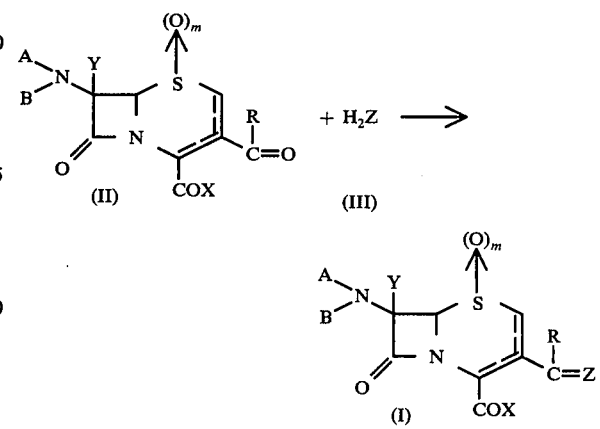

wherein A, B, X, Y, Z, R, m, and the broken line are as defined above. The compound (II) can be prepared from the corresponding 3-hydroxyalkyl compound by e.g. oxidation with chromium trioxide. Its reactive derivatives include acetals (e.g. dialkylacetal, diacyl acetal, hemiacetal, hemiacetal lactone with the carboxy at position 4) and other derivatives which form a hydrazone by the reaction with hydrazines. The hydrazine compounds (III) are easily available compounds. The reactive derivatives of the hydrazine compounds (III) include salts of the compound (III) with an acid, N-acyl derivatives (e.g. alkanoyl derivatives, carbonic acyl derivatives), alkylidene derivatives, aralkylidene derivatives, or like reactive derivatives which form hydrazones by the reaction with the oxo compounds (II) or its reactive derivatives. The reaction can be carried out by contacting the reactants, preferably in a solvent to give the desired products (I). The solvent can be a hydrocarbon, halohydrocarbon, ether, ester, alcohol, carboxylic acid, base, amide, nitrile, nitrohydrocarbon, sulfoxide, or water solvents, or their mixtures. Preferred solvents are tetrahydrofuran, tetrahydropyran, ethyleneglycol dimethyl ether, dimethylformamide, dimethylacetamide, dimethylsulfoxide, water, or their mixtures. The reaction can be carried out preferably at room temperature, or elevated or cooled temperature. The pH of the reaction medium can be adjusted to neutral or weakly acid condition for fast reaction. Stirring and protection from moisture with an inert gas, of the reaction mixture are preferable. This reaction proceeds through 3-($\alpha$-hydroxy-$\alpha$-hydrazinylalkyl)cephem compounds as intermediates. The products can be recovered by a conventional method (e.g. extraction, precipitation, adsorption, recrystallization, reprecipitation, chromatography). When the free acid is obtained, it can be converted to a salt by neutralization or cation exchange with a metal salt suitable for salt formation. (2) When A or B of the compound (I) is a hydrogen, the amino can be protected to give the compound (I) where A or B is an amino protecting group by conventional methods. Among the amino protecting group, the acyl group can be introduced with an acylating reagent having the desired acyl moiety which include halides, anhydrides, reactive esters, reactive amides, and azides, or like acylating reagents; silyl, sulfenyl, or hydrocarbon groups can be introduced with e.g. silyl halide compounds, silazanes, sulfenyl halides, halo-hydrocarbons, aldehydes, ketones, or like reagents. In these cases, the group —NAB can be activated previously in the forms of iminohalides, iminoethers, isocyanates, or like forms.

(3) The compound (I) where A or B is an amino protecting group can be deprotected to give a compound (I) where A or B is a hydrogen. The methods for deprotection include the action of carbonium ion forming reagents, acid, acid halides, toluene-p-sulfonic acid, hydrazine, and phosphorous pentachloride followed by alcohols and acids, for acyl groups; catalytic hydrogenation or reducing metals with acid for benzyloxycarbonyl or haloalkoxycarbonyl; acids or bases for silyl or sulfenyl; acids, catalytic hydrogenation, or hydrogenolytic reducing reagents for aralkyl, 1-alkylene, alkylidene, or aralkylidene; respectively according to conventional methods.

(4) The compound (I) where X is a hydroxy can be protected to give a compound (I) where X is a carboxy protecting group. The methods for protecting include esterification with alcohols or phenols or their reactive derivatives, diazo compounds, halogenated compounds, reactive ester, reactive amide, or like esterifying reagents; amide formation with amine compounds, hydrazine compounds, reactive amides, or like amidating reagents; salt formation from a free acid with a base or cation exchange with other suitable salts; and silyl or tin esters with silyl halides, disilazanes, tin halides, or like organic silyl or organic tin reactive derivatives. Prior to these protections, the carboxy group can be activated with halide forming reagents (e.g. thionyl halides, phosphorous trihalides, oxalyl halides), acylating reagents (e.g. alkoxycarbonyl halides for anhydride formation), amidating reagents (e.g. carbonyl diimidazole for reactive amide formation), esterifying reagents (e.g. p-nitrophenol for reactive ester formation), or like reagents.

(5) The compound (I) where X is a carboxy protecting group can be deprotected to give the compound (I) where X is a hydroxy. The deprotections include acid (e.g. inorganic acid, sulfonic acids, trifluoroacetic acid, or other organic acids), water, or base for esters, amides, or anhydrides; reducing reagents (e.g. zinc, tin) for haloalkyl esters; alkali metal thiophenoxides for phenacyl ester and other conventional deprotection to give the carboxy group. The salts can be liberated to give free acids by the action of an acid including cation exchange resins ($H^+$-form).

(6) The compound (I) where m is 0 can be treated with an oxidizing reagent to give the compound (I) where m is 1. The oxidizing reagent includes oxidizing inorganic salts (e.g. periodates, permanganates), inorganic or organic peracids or their salts (e.g. periodic acid, chromic acid, peralkanoic acids, aromatic percarboxylic acids, or their salts), salts, esters, or amides of hypohalogenous acids, iodobenzene salts, metal peroxides (e.g. nickel peroxide), hydrogen peroxide, oxygen, ozone, or other reagents capable of oxidizing a sulfide to give a sulfoxide. If required, regulators e.g. isopropanol, can be added to the reaction mixture.

(7) The compound (I) where $m$ is 1 can be treated with a reducing reagent to give the compound (1) where $m$ is 0. The reducing reagent includes reducing inorganic salts (e.g. thiosulfate, iodides, divalent tin or iron salts), phosphorous trihalides, phosphines, hydrides (e.g. sodium borohydride), hydrogen, or other reducing reagents capable of reducing sulfoxides to give sulfides, which can be used by the conventional methods in the art.

(8) The compound (I) where the group A, B, X, or Z has a functional group can be protected by a suitable protecting group to give the compound (I) where A, B, X, or Z has protected functional groups. The methods are conventional in the art. For example, amino is protected by an acyl group by means of an acylating reagent (e.g. acid halides, acid anhydrides, acid azides, reactive amides, reactive esters), by a silyl or sulfenyl group by means of silyl halide compounds, disilazane compounds, sulfenyl halides, or like reagents, or by a hydrocarbon group by means of unsaturated compounds, halohydrocarbons, oxo compounds, or other methods described before at item (2); hydroxy can be protected with the acylating reagent described above, with an etherifying reagent (e.g. dihydropyrane, 1,1-dialkoxyalkanes, oxo compounds) or by other reagents to protect it in the forms of esters, ethers, acetals, or other protected forms; oxo can be protected with alcohols, hydroxylamine, acylating reagents, or other reagents to protect it in the forms of acetals, oximes, enol ethers, enol esters, or other protected forms; carboxy can be protected with alcohols, diazo compounds, or like reagents to protect it in the forms of esters, or other methods described above in the item (4); basic groups and acid groups can be protected with acids or bases to protect them in the forms of salts; or other conventional methods in the art.

(9) The compound (I) where the group A, B, X, or Z has protected functional groups can be deprotected to give the compound (I) where the groups have functional groups. The deprotecting methods are conventional in the art. For example, the amino protecting group, namely acyl, silyl, sulfenyl, hydrocarbon group and like amino protecting groups can be removed by hydrolysis, hydrogenolysis, reducing reagents, ultraviolet irradiation, or other methods e.g. those described in item (3) above; the hydroxy protecting groups, namely acyl, silyl, ether or acetal groups, or like groups can be removed by hydrolysis, hydrogenolysis, reduction with zinc or tin, or other methods; carboxy protecting groups can be removed by hydrolysis with acid or base, hydrogenolysis, reductive fission, ultraviolet irradiation, or other methods e.g. those described in item (5) above; enol ether, enol ester, or acetals can be hydrolyzed with acid or base; and the salts of basic or acid groups can be liberated by neutralization.

The reactions (2) to (9) can be carried out generally at $-50°$ C to $100°$ C, if required in the presence of an acid, base, or condensing reagent, and preferably in conventional solvents.

The products of the reactions can be isolated and purified by extractions, concentration, precipitation, adsorption, washing, reprecipitation, recrystallization, chromatography, lyophilization, counter-current distribution, or other conventional methods.

The compounds (I) prepared by this invention are novel compounds useful as antibacterials or their intermediates. For example, the compound (I) where A is arylacetyl, B is a hydrogen, X is a hydroxy, Y and R are hydrogens, m is 0, the broken line shows the presence of a double bond at position 3, and Z is the group $=N-NHR^4$ (in which $R^4$ is an acyl containing 1 to 6 carbon atoms e.g. alkanoyl, oxalyl, alkoxalyl, or cyanoacetyl; or a carboxyphenyl), and their alkali metal salts show stronger antibacterial activity in vitro against *Proteus mirabilis* or other Gram negative bacteria than commercial cefalotin, cefaloridin, cefalexin and cefazolin. Further, the compound (I) where $R^4$ is formyl, acetyl, cyanoacetyl, oxalyl, or like groups show stronger antibacterial activity in vivo than cefalotin, cefaloridin, cefalexin, cefaloglycin, or cefazolin against *Streptococcus pyogenes* by the anti-infection test.

These antibacterial compounds can be used for the treatment or prevention of human, veterinary or plant diseases; or for disinfection or prevention of decay. For human use, they are administered as powders, solutions, vials, injections, capsules, tablets, ointments or like preparations containing 0.01 to 100% of the compounds at a daily dosage of 1 mg to 1 g per kilogram of body weight.

Among the compounds (I), 1-oxides, 2-cephems, and the usual esters are weak antibiotics useful rather as intermediates for the synthesis of the stronger antibacterials. Further, the compounds (I) where A or B is an organic acyl, inorganic acyl, or phenylthio groups are strong antibacterials against Gram positive bacteria.

The following examples represent presently preferred embodiments of this invention, but it is to be understood that the examples are given by way of illustration only and not of limitation. The elemental analyses of the compounds as prepared show good agreement with the calculated values. DMSO is for dimethyl sulfoxide, and EtOH is for ethanol.

EXAMPLE I-1.

A solution of 3-formyl-7-acylamino-3-cephem-4-carboxylic acid hemiacetal lactone (II) in an organic solvent is mixed with a solution of a hydrazine compound (III) and acid or a salt of hydrazine compound (III) in water, and left to react at room temperature. The crystals obtained by concentration of the reaction mixture are collected by filtration, washed with water and ethyl acetate or there, and dried to give the objective cephalosporin compound (I). When no or only a small amount of solid is formed on concentration, the concentrated reaction mixture or filtrate is extracted with ethyl acetate, washed with water, dried and evaporated to dryness to give a residue, which is triturated in ether or petroleum ether to obtain the desired cephalosporin compound (I).

The Tables show examples of the reaction, their reaction conditions and physical constants of their products. THF is for tetrahydrofuran and "on" means standing overnight.

EXAMPLE I-2.

In a procedure similar to that described in Example I-1, the following compounds are prepared:

(1) 3-(2-acetylhydrazono)methyl-7-(2-furylamino)-3-cephem-4-carboxylic acid, (2) 3-(2-acetylhydrazono)methyl-7-phenylacetamido-3-cephem-4-carboxylic acid, (3) 3-(2-acetylhydrazono)methyl-7-phthalimido-3-cephem-4-carboxylic acid, (4) 3-(2-acetylhydrazono)methyl-7-(2,2,2-trichloroethoxycarbonyl)-amino-3-cephem-4-carboxylic acid, (5) 3-(2-acetylhydrazono)methyl-7-benzalamino-3-cephem-4-carboxylic acid, (6) 3-(2-formylhydrazono)methyl-7-(1-tetrazolyl)acetamido-3-cephem-4-carboxylic acid, (7) 3-(2-ethoxyalylhydrazono)methyl-7-phenylglycylamino-3-cephem-4-carboxylic acid, (8) 3-(2-cyanoacetylhydrazono)methyl-7-(α-carboxyphenylacetamido)-3-cephem-4-carboxylic acid,

(90) 3-(2-cyanoacetylhydrazono)methyl-7-mandeloylamino-3-cephem-4-carboxylic acid, and

(10) 3-(2-propylhydrazono)methyl-7-mandeloylamino-3-cephem-4-carboxylic acid.

EXAMPLE I-3.

To a solution of diphenylmethyl 3-formyl-7-(2-thienylacetamido)-3-cephem-4-carboxylate (155 mg) in tetrahydrofuran (15 ml) is added a solution of carbethoxymethylhydrazine hydrochloride (69 mg) in water (2.5 ml), and the mixture is kept at room temperature for 2 days. The crystals obtained by concentration of the reaction mixture are collected by filtration, washed with ether and water, and dried to give diphenylmethyl 7-(2-thienylacetamido)-3-(2-carbethoxymethylhydrazono)methyl-3-cephem-4-carboxylate (129 mg). m.p. 70°–75° C. Yield: 69%. IR: $\nu_{max}^{Nujol}$ 3270, 1780, 1745, 1670; 1540cm$^{-1}$. NMR: $\delta^{d6-DMSO}$(60MHz) 1.435 (6Hz) 3H, 3.52ABq (24; 17Hz) 2H, 3.48s2H, 3.60s2H, 4.17 quintet (6Hz) 2H, 4.95d(5Hz)1H, 5.70dd(8;4Hz)1H, 6.67–7.63m16H, 8.03s1H. $[\alpha]_D^{24.5}$ $-144°$ (c=0.340, CHCl$_3$).

EXAMPLE I-4.

To a solution of diphenylmethyl 3-formyl-7-(2-thienylacetamido)-3-cephem-4-carboxylate (155 mg) in tetrahydrofuran (15 ml) is added a solution of (sulfolane-3-yl) hydrazine (70 mg) and 1.5 equivalents of hydrochloric acid in water (3 ml), and the mixture is kept at room temperature 5 hours. The crystals obtained by concentration of the reaction mixture are collected by filtration, washed with ether and water, and dried to give diphenylmethyl 3-(sulfolan-3-ylhydrazono)methyl-7-(2-thienylacetamido)-3-cephem-4-carboxylate (142 mg). m.p. 117°–125° C. Yield: 76%. IR: $\nu_{max}^{Nujol}$ 3275, 1785, 1715, 1675, 1530cm$^{-1}$.

EXAMPLE I-5.

To a solution of 3-formyl-7-(2-thienylacetamido)-7-methoxy-3-cephem-4-carboxylic acid hemiacetal lactone (115 mg) in tetrahydrofuran (9 ml) is added a solution of p-carboxyphenylhydrazine hydrochloride (84.8 mg) in water (3 ml), and the mixture is kept at room temperature for 3 hours. The crystals obtained by concentration of the reaction are collected by filtration, washed with ether and water, and dried to give 3-(2-p-carboxyphenylhydrazono)methyl-7-(2-thienylacetamido)-7-methoxy-3-cephem-4-carboxylic acid monohydrate (87 mg). m.p. 156°–162° C (decomposition). Yield: 56%. IR: $\nu_{max}^{Nujol}$ 3260, 1770, 1681, 1605, 1533cm$^{-1}$. UV: $\lambda_{max}^{EtOH}$ 236nm ($\epsilon$=15100); 288nm ($\epsilon$=6900). NMR: $\delta^{d6-DMSO}$ 3.39S2H, 3,39s3H, 3.85s2H, 5.25s1H, 6.9–7.5m3H, 8.30s1H, 9.78s1H, 12.80s1H. $[\alpha]_D^{23}$ −78.6° (c=0.280, DMSO).

EXAMPLE I-6

To a solution of 3-formyl-7-(2-thienylacetamido)-7-methoxy-3-cephem-4-carboxylic acid hemiacetal lactone (115 mg) in tetrahydrofuran (9 ml) is added a solution of acetylhydrazine (44.4 mg) in water (3 ml) containing hydrogen chloride (2 equivalents), and the mixture is kept at room temperature overnight. The reaction mixture is concentrated to give oily materials, which are extracted with ethyl acetate. The extract solution is washed with water, dried and evaporated. The obtained residue, is triturated in ether to give 3-(2-acetylhydrazono)methyl-7-(2-thineylacetamido)-7-methoxy-3-cephem-4-carboxlyic acid (68 mg). m.p. 173–176° C (decomposition). Yield: 52% IR: $\nu_{max}^{Nujol}$ 3260, 1788, 1714, 1675, 1597 (Shoulder), 1535, 1525cm$^-$. UV: $\lambda_{max}^{EtOH}$ 234nm($\epsilon$=13400); 319nm($\epsilon$=21300). NMR: $\delta^{d6-DMSO}$ (60MH$_z$)1.92s+ 2.12s3H, 3.40s3H, 3.74d(5Hz)2H, 3.83s2H, 5.25s1H, 6.90–7.45m 3H, 8.12s+8.28s1H, 9.48s1H. $[\alpha]_D^{23.5}$ +125° (c=0.305, DMSO).

EXAMPLE I-7.

In a procedure similar to that described in Example I-3, diphenylmethyl 3-formyl-7-(2-thienylacetamido)-2-cephem-4-carboxylate (104 mg) and acetylhydrazine (30 mg) are left to react in a mixture of tetrahydrofuran (8 ml) and water (1.5 ml) in the presence of hydrochloric acid (2 equivalents) at room temperature overnight to give diphenylmethyl 3-(2-acetylhydrazono)methyl-7-(2-thienylacetamido)-2-cephem-4-carboxylate (95 mg). m.p. 168–178° C (decomposition). Yield: 83%. IR: $\lambda_{max}^{Nujol}$3280, 1760, 1743, 1695, 1667, 1697, 1677, 1538cm$^{-1}$. UV: $\lambda_{max}^{EtOH}$ 301nm($\epsilon$=31700). NMR: $\delta^{CDCl_3}$ (60MHz) 1.82s3H, 3.82s2H, 5.07d(4Hz)1H, 5.40s1H, 5.50br1H, 6.63br1H, 6.83s1H. 6.88-7.58m15-16H. $[\alpha]_D^{23}$ +416° (c=0.501, CHCl$_3$).

EXAMPLE I-8.

In a procedure similar to that described in Example I-3, diphenylmethyl 3-formyl-7-(2-thienylacetamido)-3-cephem-4-carboxylate 1-oxide (107 mg) and acetylhydrazine (30 mg) are left to react in a mixture of tetrahydrofuran (8 ml) and water (1.5 ml) in the presence of hydrochloric acid (2 equivalents) at room temperature overnight to give diphenylmethyl 3-(2-acetylhydrazono)-methyl-7-(2-thienylacetamido)-3-cephem-4-carboxylate 1-oxide (104 mg). m.p. 205°–214° C (decomposition). Yield: 88%. IR: $\nu_{max}^{Nujol}$3270, 1787, 1722, 1675, 1690, 1530cm$^{-1}$. UV: $\lambda_{max}^{EtOH}$ 329nm($\epsilon$=22530). NMR: $\delta^{d6-DMSO}$ (60MHz) 1.92s+2.13s3H, 3.88 s2H, 5.05d(4Hz)1H, 5.98dd(4;9Hz)1H, 6.82-7.72m14H, 8.37s+8.52s2H, 11.45d(9Hz)1H. $[\alpha]_D^{23}$ −234° (c+0.487, CHCl$_3$)

EXAMPLE I-9.

In a procedure similar to that described in Example I-3, diphenylmethyl 3-formyl-7-(2-thienylacetamido)-3-cephem-4-carboxylate (104 mg) and acetylhydrazine (30 mg) are left to react in a mixture of tetrahydrofuran (8 ml) and water (1.51 ml) in the presence of hydrochloric acid (2 equivalents) at room temperature overnight to give diphenylmethyl 3-(2-acetylhydrazono)methyl-7-(2-thienylacetamido)-3-cephem-4-carboxylate (101 mg). m.p. 130-138° C. Yield: 88%. IR: $\nu_{max}^{Nujol}$ 3250, 1782, 1715, 1670, 1597, 1535 cm$^{-1}$. UV: $\lambda_{max}^{EtOH}$327nm($\epsilon$=24000). NMR: $\delta^{CDCl_3}$ (60MHz) 220s3H, 3.72ABq(39;18Hz)2H, 3.82s2H, 5.00d(5Hz)1H, 5.87dd (9;5Hz)1H, 6.77-7.58ml5H, 8.05s1H, 9.65s1H. $[\alpha]_D^{23}$ −258° (c=0.493,CHCl$_3$).

EXAMPLE II-1

A solution (2 ml) of 2-thienylacetyl chloride prepared from 2-thienylacetic acid (78 mg) and thionyl chloride (0.05 ml) in chloroform is added dropwise to a solution of 7-amino-3-(2-ethoxylalylhydrazono)methyl-3-cephem-4-carboxylic acid (171 mg) and triethylamine (0.14 ml) in chloroform (2 ml), and the mixture is stirred for 1 hour. The residue obtained by concentration of the reaction mixture is dissolved in a mixture of water and ether. The aqueous layer is acidified with 10% hydrochloric acid to pH 1.5, and extracted with ethyl acetate. The extract solution is washed with water and dried, and concentrated. The obtained residue is crystallized from a mixture of ether and ethyl acetate to give 7-(2-thienylacetamido)-3-(2-ethoxyalylhydrazono)methyl-3-cephem-4-carboxylic acid monohydrate (196 mg). m.p. 134-137° C (decomposition). Yield: 84%.

EXAMPLE II-2.

A mixed an anhydride prepared from 2-thienylacetic acid (78 mg), isobutyl chloroformate (0.07 ml), and triethylamine (0.08 ml) is added to a solution of 7-amino-3-(2-acetylhydrazono)-methyl-3-cephem-4-carboxylic acid (124 mg) and triethylamine (0.07 ml) in tetrahydrofuran (6 ml) under ice cooling. After standing for 6 hours at room temperature, the reaction mixture is concentrated, and the residue is dissolved in a mixture of ethyl acetate and water. The aqueous layer is washed with a small amount of ethyl acetate, acidified to pH 2 with hydrochloric acid, and extracted with ethyl acetate. The extract solution is dried and evaporated. The obtained residue is triturated in ether to give 7-(2-thienylacetamido)-3-(2-acetylhydrazono)methyl-3-cephem-4-carboxylic acid monohydrate (121 mg). m.p. 184°–190° C (decomposition). Yield: 65%.

EXAMPLE II-3.

A solution of 2,4-dinitrophenyl 2-thienylacetate (prepared from 2-thienylacetic acid (31 mg), 2,4-dinitrophenol (40 mg) and N,N'-dicyclohexylcarbodiimide (36 mg), in tetrahydrofuran (0.5 ml) in chloroform (0.2 ml) is added into a solution of 7-amino-3-(2-formylhydrazone)-methyl-3-cephem-4-carboxylic acid (40 mg) and triethylamine (0.09 ml) in chloroform (0.5 ml). After 15 hours stirring, the reaction mixture is concentrated to give a residue which is dissolved in water, washed with ethyl acetate, acidified to pH 2 with hydrochloric acid, and extracted with ethyl acetate. The dried extract is concentrated. The obtained residue is triturated in ether to give 7-(2-thienylacetamido)-3-(2-formylhydrazono)methyl-3-cephem-4-carboxylic acid monohydrate (52 mg). m.p. 150°–160° C (decomposition). Yield: 72%.

EXAMPLE II-4.

To a solution of 7-amino-3-(2-pyridyl)hydrazonomethyl-3-cephem-4-carboxylic acid (106 mg) and triethylamine (51 mg) in dimethylsulfoxide (0.5 ml) is added N-carbethoxyphthalimide (80 mg), and the mixture is stirred for 24 hours. The reaction mixture acidified to pH 2 with hydrochloric acid is shaken with water and ethyl acetate. The aqueous layer is saturated with sodium sulfate and extracted with ethyl acetate. The dried extract solution is concentrated to give a residue which is triturated in ether to give 7-phthalimido-3-(2-pyridyl)hydrazono-methyl-3-cephem-4-carboxylic acid (106 mg). Yield 71%.

EXAMPLE II-5.

To a solution of diphenylmethyl 7-amino-3-(2-ethoxalylhydrazono)methyl-3-cephem-4-carboxylate (127 mg) and 2-thienylacetic acid (36 mg) in tetrahydrofuran (3 ml) is added N,N'-dicyclohexylcarbodiimide (54 mg) and stirred for 4 hours. The separated precipitate is removed by filtration, and concentrated to give a residue which is extracted with methylene chloride. The extract solution is concentrated and triturated in a mixture of ether and ethyl acetate to give diphenylmethyl 7-(2-thienylacetamido)-3-(2-ethoxyalyldrazono)methyl-3-cephem-4-carboxylate (112 mg). Yield: 71%.

EXAMPLE II-6.

The compounds prepared by the procedures of Examples I-1 to 9 are preparable by the methods similar to Examples II-1 to 5.

EXAMPLE III-1.

To a solution of sodium 3-(2-acetylhydrazone)methyl-7-(o-nitrophenylsulfenyl)amino-3-cephem-4-carboxylate (100 mg) in 75% dioxane (5 ml) is added hydrochloric acid and potassium iodide to adjust it to pH 3, and the separated iodine is titrated with sodium thiosulfate. The reaction mixture is acidified to pH 1.5 with hydrochloric acid, washed with ether, neutralized and extracted with ethyl acetate. The extract solution is washed with water, dried and evaporated to give 7-amino-3-(2-acetylhydrazono)methyl-3-cephem-4-carboxylic acid.

EXAMPLE IV-1.

To a solution of 3-(2-acetylhydrazone)methyl-7-(2-thienylacetamido)-3-cephem-4-carboxylic acid (75 mg) in a mixture of methylene chloride and methanol is added a solution of diphenyldiazomethane in petroleum ether, and the mixture is kept at room temperature for 13 hours. The reaction mixture is concentrated to give a residue which is dissolved in ethyl acetate and diluted with ether. The separated crystals are collected by filtration, washed with ether, and dried to give dephenylemthyl 3-(2-acetylhydrazono)methyl-7-(2-thienylacetamido)-3-cephem-4-carboxylate (87 mg). m.p. 130°–138° C. Yield: 78%.

In a manner similar to that described above, 3-(2-acetylhydrazone)methyl-7-(2-thienylacetamido)-3-cephem-4-carboxylic acid 1-oxide is esterified to give the corresponding diphenylmethyl ester.

EXAMPLE V-1.

To a solution of diphenylmethyl 3-(2-carbethoxymethyl-hydrazono)methyl-7-(2-thienylacetamido)-3-cephem-4-carboxylate (108 mg) in methylene chloride (2 ml) are added anisol (0.1 ml) and trifluoroacetic acid (0.2 ml), and the mixture is kept at 0° C for 2 hours. The reaction mixture is concentrated to remove methylene chloride and trifluoroacetic acid, and the obtained residue is diluted with ether. The separated crystals are collected by filtration to give 7-(2-thienylacetamido)-3-(2-carbethoxymethylhydrazone)methyl-3-cephem-4-carboxylic acid (61 mg). m.p. 126°–135° C (decomposition). Yield: 77%. IR: $\nu_{max}^{Nujol}$ 3270, 745, 1665, 1605, 1540 cm$^{-1}$. UV: $\nu_{max}^{EtOh}$ 345nm ($\epsilon=12000$).

EXAMPLE V-2.

To a solution of diphenylmethyl 3-(sulfolane-3-yl-hydrazono)methyl-7-(2-thienylacetamido)-3-cephem-4-carboxylate (122 mg) in methylene chloride (2 ml) are added anisol (0.1 ml) and trifluoroacetic acid (0.2 ml), and the mixture is kept a 0° C for 2 hours. The reaction mixture is concentrated to remove methylene chloride and trifluoroacetic acid, and the obtained residue is diluted with ether. The separated crystals are collected by filtration, washed with ethyl acetate and water, and dried to give 3-(sulfolan-3ylhydrazone)methyl-7-(2-thienylacetamido)-3-cephem-4-carboxylic acid (110 mg). m.p. 140°–150° C (decomposition). Yield: 91%. IR: $\nu_{max}^{Nujol}$ 3500, 3280, 1790, 1660, 1605, 1530cm$^{-1}$. UV: $\lambda_{max}^{EtOH}$ 228nm($\epsilon=15250$); 317nm ($\epsilon=7600$); 400nm($\epsilon=37000$). NMR: $\delta^{d}$6-DMSO 3.0–4.4m8H, 3.83s2H, 5.20d(5Hz)1H, 5.97dd(8.5Hz)2H, 6.77–7.60, 8.00s1H, 9.13d(8Hz)1H. $[\alpha]_D^{25}$ +107° (c=0.303, DMSO).

EXAMPLE VI-1.

To a solution of diphenylmethyl 7-(2-thienylacetamido)-3-(2-acetylhydrazono)methyl-2-cephem-4-carboxylate (188 mg) in methylene chloride (4 ml) is added dropwise a solution of m-chloroperbenzoic acid (60 mg) in a mixture of methylene chloride (0.6 ml) and isopropanol (0.6 ml). After 1 hour, the reaction mixture is diluted with methylene chloride and petroleum ether. The separated precipitate is collected by filtration, washed with methylene chloride, and dried to give diphenylmethyl 7-(2-thienylacetamido)-3-(2-acetylhydrazone)methyl-3-cephem-4-carboxylate 1-oxide (184 mg). m.p. 205°–214° C (decomposition). Yield: 95%.

In a method similar to that described above, diphenylmethyl 7-(2-thienylacetamido)-3-(2-acetylhydrazono)methyl-3-cephem-4-carboxylate is oxidized with m-chloroperbenzoic acid to give a compound identical with the compound prepared by the method described above.

EXAMPLE VI-2.

An aqueous solution of 0.25M periodic acid (2.5 ml) diluted with a phosphate buffer (pH 6; 3.8 ml) is added to a solution of diphenylmethyl 7-(2-thienylacetamido)-3-(2-formylhydrazono)methyl-3-cephem-4-carboxylate (183 mg) in dioxane (8 ml), and the mixture is stirred at room temperature for 3 hours. The reaction mixture evaporated to remove dioxane is extracted with ethyl acetate. The extract solution is washed with water, dried, and concentrated. The obtained residue is crystallized from a mixture of ethyl acetate and ether giving diphenylmethyl 7-(2-thienylacetamido)-3-(2-formylhydrazono)-methyl-3-cephem-4-carboxylate 1-oxide (113 mg). Yield: 60%.

EXAMPLE VII-1.

To a solution of stannous chloride dihydrate (112 mg) and diphenylmethyl 7-(2-thienylacetamido)-3-(2-acetylhydrazono)-methyl-3-cephem-4-carboxylate 1-oxide (145 mg) in N,N-dimethylformamide (4 ml) is added acetyl chloride (0.18 ml) under ice cooling. After stirring for 2 hours, the reaction mixture is diluted with ice water and extracted with ethyl acetate. The extract solution is washed with a dilute aqueous solution of sodium hydrogen carbonate and water, and driec, and is concentrated to give a residue which is triturated in a mixture of ethyl acetate and ether. The separated precipitate is collected by filtration and dried to give diphenylmethyl 7-(2-thienylacetamido)-3-(2-acetylhydrazono)methyl-3-cephem-4-carboxylate (118 mg). m.p. 130°–138° C. Yield: 84%.

EXAMPLE VIII-1.

A solution of 3-hydrazonomethyl-7-(2-thienylacetamido)-3-cephem-4-carboxylic acid (93 mg) in a mixture of acetic anhydride (0.5 ml) and pyridine (0.2 ml) is kept at room temperature for 45 hours. The mixture is diluted with ether. The obtained precipitate is collected by filtration and dried to leave 3-(2-acetylhydrazono)methyl-7-(2-thienylacetamido)-3-cephem-4-carboxylic acid monohydrate (101 mg). m.p. 184°–190° C (decomposition). Yield: 96%.

EXAMPLE IX-1.

To a solution of 3-(2-tertiary butoxycarbonylhydrazono)methyl-7-(2-thienylacetamido)-3-cephem-4-carboxylic acid (247 mg) in methylene chloride (1 ml) are added anisole (0.6 ml) and trifluoroacetic acid (0.6 ml), and the mixture is kept at room temperature for 1 hour. After removing trifluoroacetic acid and methylene chloride, the reaction mixture is diluted with ether. The separated cyrstals are collected by filtration and dried to give 3-hydrazonomethyl-7-(2-thienylacetamido)-3-cephem-4-carboxylic acid in nearly quantitative yield. m.p. 164°–169° C (decomposition). IR: $\nu_{max}^{Nujol}$ 3260, 1787, 1657, 1542cm$^{-1}$. UV: $\lambda_{max}^{CH_3OH}$ 230.5nm($\epsilon$=12900); 304nm($\epsilon$=6900); 402nm($\epsilon$=12400). NMR: $\delta^{d_6\text{-}DMSO}$(60MHz) 3.79s2H, 3,84d(12Hz)2H, 5.20d(5Hz)1H, 5.84dd(8;5Hz)1H, 6.8-7.5m3H, 7.55s+7.78s1H, 9.12d(8Hz)1H. $[\alpha]_D^{23.5}$ +66.2°(c=0.5022, DMSO).

EXAMPLE IX-2.

A solution of 3-[2-(N-tertiary butoxycarbonylglycyl)-hydrazono]methyl-7-(2-thienylacetamido)-3-cephem-4-carboxylic acid (120 mg) in a mixture of anisole (0.6 ml) and trifluoroacetic acid (1.2 ml) is kept at 0° C for 1 hour. The reaction mixture is concentrated to remove trifluoroacetic acid, and the obtained residue is diluted with ether. The separated crystals are washed with ether and water and dried to give 3-(2-glycylhydrazono)methyl-7-(2-thienylacetamido)-3-cephem-4-carboxylic acid (60 mg). m.p. 204°–209° C (decomposition). Yield: 62%. IR: $\nu_{max}^{Nujol}$ 3260, 1767, 1660, 1600, 1585cm$^{-1}$. UV: $\nu_{max}^{EtOH}$ 235nm; 316nm (Saturated solution). NMR: $\delta^{d_6\text{-}DMSO}$ 3.58s2H, 3.9dd2H, 5.17d(4Hz)1H, 5.75dd(8;4Hz)1H, 6.80–7.47m3H, 8.20s1H, 9.13d(8Hz)1H.

| No. | (II) Acyl (mg) | (III) =Z (Mg) | Solvent (ml) | Acid (equivalent) | Reaction Time (hrs) | Crop (mg) | Yield (%) | No. |
|---|---|---|---|---|---|---|---|---|
| 1 | thienyl-CH₂CO— (141) | =NNH₂ HCl (30) | THF+H₂O 14+4 | — | 2 | 126 | 86 | 1 |
| 2 | thienyl-CH₂CO— (141) | =NNH—C₆H₅ (65) | THF+H₂O 12+4.6 | HCl 1.5 | 2 | 140 | 79 | 2 |
| 3 | thienyl-CH₂CO— (141) | =NN(CH₃)(C₆H₅) (73.2) | THF+H₂O 12+4.6 | HCl 1.5 | on | 112 | 61.5 | 3 |
| 4 | thienyl-CH₂CO— (141) | =NNH—C₆H₄—COOH (91) | THF+H₂O 12+4.6 | HCl 1.5 | 3 | 168 | 86 | 4 |

-continued

| | (II) | (III) | Solvent | Acid | Reaction | (I) | | (I) |
| No. | Acyl (mg) | =Z (Mg) | (ml) | (equivalent) | Time (hrs) | Crop (mg) | Yield (%) | No. |
|---|---|---|---|---|---|---|---|---|
| 5 | thienyl-CH₂CO— (141) | =NNH-C₆H₃(COOH)(HCl) (112.5) | THF+H₂O 12+5 | — | 2.5 | 150 | 77 | 5 |
| 6 | thienyl-CH₂CO— (143) | =NNH-C₆H₄-SO₂CH₃ (113) | THF+H₂O 14+2.7 | HCl 1.5 | 5 | 152 | 73 | 6 |
| 7 | thienyl-CH₂CO— (141) | =NNH-C₆H₄-SO₃Na (92.4) | THF+H₂O 12+8.7 | CH₃COOH 1.1 | 2.5 | 185 | 85 | 7 |
| 8 | thienyl-CH₂CO— (141) | =NNH-pyridyl·2HCl (109) | THF+H₂O 12+5 | — | 48 | 88 | 50 | 8 |
| 9 | thienyl-CH₂CO— (142) | =NN-(N-CH₃-pyridinium)·HCl (118) | THF+H₂O 14+2.5 | — | 3 | 74 | 40 | 9 |
| 10 | thienyl-CH₂CO— (141) | =NNH-thiazolyl (69) | THF+H₂O 12+4.6 | HCl 1.5 | on | 138 | 77 | 10 |
| 11 | thienyl-CH₂CO— (142) | =NNH-(4-amino-5-mercapto-triazolyl) (88) | THF+H₂O 14+7.3 | HCl 8 | 4 | 134 | 70 | 11 |
| 12 | thienyl-CH₂CO— (141) | =NNH—(Purin-6-yl) (90) | THF+H₂O 14+3.1 | HCl 1.5 | 21 | 113 | 58 | 12 |
| 13 | thienyl-CH₂CO— (141) | =NNH-(sulfolanyl) (64) | THF+H₂O 14+3 | — | 3 | 136 | 73.5 | 13 |
| 14 | thienyl-CH₂CO— (141) | =NNHCH₂COOC₂H₅ (49) | THF+H₂O 14+4 | HCl 1.5 | 5 | 153 | 87 | 14 |
| 15 | thienyl-CH₂CO— (177) | =NNHCHO (46.6) | THF+H₂O 20+3.3 | HCl 1.5 | 2.6 | 33 | 17 | 15 |
| 16 | thienyl-CH₂CO— (141) | =NNHC(O)CH₃ (44.4) | THF+H₂O 12+4.6 | HCl 1.5 | on | 130 | 80 | 16 |
| 17 | thienyl-CH₂CO— (141) | =NNHCOCH₂NH₂·HCl (53) | THF+H₂O 14+3.5 | — | 11 | 149 | 83 | 17 |
| 18 | thienyl-CH₂CO— (290) | =NNHC(O)CH₂NH·COOC₄H₉ (234) | THF+H₂O 30+1.3 | HCl 1.5 | 1 | 317 | 74 | 18 |
| 19 | thienyl-CH₂CO— (64.8) | =NNHC(O)CH₂N⁺(CH₃)₃ Cl⁻ (34) | THF+H₂O 1.5+0.3 | — | 1.75 | 64 | 69.4 | 19 |
| 20 | thienyl-CH₂CO— (78.6) | =NNHC(O)CH₂N⁺-pyridyl Cl⁻ (46) | THF+H₂O 1.9+0.4 | — | 4 | 115 | 98.8 | 20 |

-continued $$\underset{(II)}{\text{Acyl-NH}\underset{O}{\overset{S}{\underset{N}{\bigsqcup}}}\underset{CO}{\overset{CH-OH}{\underset{\bigsqcup}{\bigsqcup}}}} \xrightarrow[\text{room temperature}]{H_2Z \text{ (III)}} \underset{(I)}{\text{Acyl-NH}\underset{O}{\overset{S}{\underset{N}{\bigsqcup}}}\underset{COOH}{\overset{CH=Z}{\bigsqcup}}}$$

| No. | (II) Acyl (mg) | (III) =Z (Mg) | Solvent (ml) | Acid (equivalent) | Reaction Time (hrs) | (I) Crop (mg) | (I) Yield (%) | No. |
|---|---|---|---|---|---|---|---|---|
| 21 | ⟨S⟩-CH₂CO— (141) | =NNHCOCOOK (142) | THF+H₂O 12+4 | HCl 3 | 2 | 85 | 49 | 21 |
| 22 | ⟨S⟩-CH₂CO— (141) | =NNHCOCOOC₂H₅ (133) (COOH)₂ | THF+H₂O 12+5 | — | 2 | 130 | 70 | 22 |
| 23 | ⟨S⟩-CH₂CO— (141) | =NNHCOCONH₂ (61.8) | THF+H₂O 12+4 | HCl 1.5 | 2 | 92 | 52.5 | 23 |
| 24 | ⟨S⟩-CH₂CO— (141) | =NNHCOCONHNH₂ (71) | THF+H₂O 12+4 | HCl 1.5 | 1.5 | 118 | 65 | 24 |
| 25 | ⟨S⟩-CH₂CO— (141) | =NNHCCH₂CN (59) ‖ O | THF+H₂O 12+4.6 | HCl 1.5 | on | 138 | 78.5 | 25 |
| 26 | ⟨S⟩-CH₂CO— (141) | =NNHC(O)-C(H)(OH)-C(OH)(H)-C(OH)(H)-CH₂OH (84) | THF+H₂O 12+6.6 | CH₃COOH 1.1 | 1 | 175 | 80 | 26 |
| 27 | ⟨S⟩-CH₂CO— (70.5) | =NNHCO-C₆H₅ (54.5) | THF+H₂O 8+2.4 | HCl 2 | 5 | 82 | 87 | 27 |
| 28 | ⟨S⟩-CH₂CO— (70.5) | =NNHCO-(4-pyridyl) (55) | THF+H₂O 8+2.4 | HCl 2 | 5.5 | 72 | 77 | 28 |
| 29 | ⟨S⟩-CH₂CO— (143) | =NNHCO-(2-furyl) (76) | THF+H₂O 14+2.7 | HCl 1.5 | 2.5 | 130 | 71 | 29 |
| 30 | ⟨S⟩-CH₂CO— (142) | =NNHCO-(isoxazolyl) (76) | THF+H₂O 14+0.6 | HCl 1.5 | 2 | 121 | 66 | 30 |
| 31 | ⟨S⟩-CH₂CO— (142) | =NNHCO-(5-methyl-isoxazolyl) (85) | THF+H₂O 14+0.6 | HCl 1.5 | 2 | 139 | 73 | 31 |
| 32 | ⟨S⟩-CH₂CO— (141) | =NNHCO-(thiazolyl) (86) | THF+H₂O 12+4.6 | HCl 1.5 | 2.5 | 154 | 80.5 | 32 |
| 33 | ⟨S⟩-CH₂CO— (141) | =NNHCO-(5-methyl-1,3,4-thiadiazolyl) (95) | THF+H₂O 12+4.6 | HCl 1.5 | 2.5 | 157 | 80 | 33 |
| 34 | ⟨S⟩-CH₂CO— (142) | =N-N(pyridazinone)·HCl (120) | THF+H₂O 14+2 | — | 120 | 19 | 10 | 34 |
| 35 | ⟨S⟩-CH₂CO— (141) | =NNHSO₂-C₆H₄-CH₃ (111.5) | THF+H₂O 12+4.6 | HCl 1.5 | 28 | 142 | 68 | 35 |
| 36 | ⟨S⟩-CH₂CO— (141) | =NNHCOOCH₃ (54) | THF+H₂O 14+3 | HCl 1.5 | 4 | 138 | 82 | 36 |

-continued
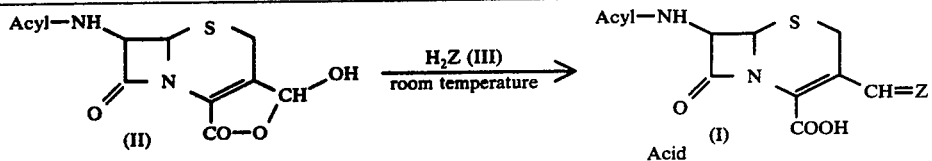
| No. | (II) Acyl (mg) | (III) =Z (Mg) | Solvent (ml) | Acid (equivalent) | Reaction Time (hrs) | (I) Crop (mg) | (I) Yield (%) | No. |
|---|---|---|---|---|---|---|---|---|
| 37 | ![thiophene]-CH₂CO— (141) | =NNHCOOC₄H₉-t (79.2) | THF+H₂O 14+3.6 | HCl 1.5 | 3 | 152 | 84.5 | 37 |
| 38 | ![thiophene]-CH₂CO— (141) | =NNHCSSCH₃ (97.7) | THF+H₂O 14+3.3 | HCl 1.5 | 17 | 126 | 69 | 38 |
| 39 | ![thiophene]-CH₂CO— (200) | =NNH-(imidazolidinone) HI (277) | THF+H₂O 17+6 | — | on | 190 | 74.5 | 39 |

| No. | Acyl | =Z | m.p. | IR-spectrum $\nu_{max}^{Nujol}$ cm$^{-1}$ | UV-spectrum $\nu_{max}^{EtOH}$ nm (ε) | NMR-spectrum $\delta^{DMSO}_{d_6}$ (60 MHz) | $[\alpha]_D^t$ °C(c) |
|---|---|---|---|---|---|---|---|
| 1 |  | =NNH$_2$ | 164–169° C (dec.) | 3260,1787,1657, 1542. | 230,5(12900), 304(6900), 402(12400). | 3.79s2H,3.84d(12Hz)2H,5.20d(5Hz)1H,5.84 dd(8;5Hz)1H,6.8–7.5m3H,7.55,7.78s+s1H, 9.12d(8Hz)1H. | +66.2° 0.502DMSO 23.5° C |
| 2 |  | =NNH—⟨phenyl⟩ ¼H$_2$O | 152–156° C (dec.) | 3280,1772,1715, 1695,1655,1602, 1534. | 237(15900), 366(26900). CH$_3$OH | 3.80s2H,3.97ABq(32;17Hz)2H,5.17d(4.5Hz) 1H,5.67dd(8.4.5Hz)1H,6.8–7.6m8H,8.27s1H, 9.09d(8Hz)1H,12.35s1H. | −247.8° 0.3686CH$_3$OH 24° C |
| 3 |  | =NN(CH$_3$)—⟨phenyl⟩ ¼H$_2$O | 175–183° C (dec.) | 3265,1777,1707, 1698,1596. | 236(12600), 350(29000). CH$_3$OH | 3.34s3H,3.81s2H,4.00ABq(32;17Hz)2H,5.18 d(5Hz)1H,5.69dd(8;5.5Hz)1H,6.8–7.5m8H,8 8.01s1H,9.10d(8Hz)1H. | −151.2° 0.183CH$_3$OH 24° C |
| 4 |  | =NNH—⟨C$_6$H$_4$⟩COOH | 170–175° C (dec.) | 3260,1776,1680, 1605,1535. | 235(17400), 373(40000). CH$_3$OH | 3.80s2H,5.19d(4.5Hz)1H,5.70dd(8;4.5Hz) 1H,6.8–8.0m7H,8.27s1H,9.10d(8Hz)1H, 12.70s1H. | −323.8° 0.3050DMSO 24.5° C |
| 5 |  | =NNH—⟨C$_6$H$_4$⟩(HOOC) | 177–180° C (dec.) | 3260,1770,1662, 1590,1540,1515. | 222(23500), 375(26900). CH$_3$OH | 3.80s2H,3.99ABq(36;18Hz)2H,5.21d(5Hz) 1H,5.73dd(8;5Hz)1H,6.8–8.0m7H,8.23s1H, 9.12d(8Hz)1H,12.98s1H. | −125.0° 0.0712CH$_3$OH 24° C |
| Δ6 |  | =NNH—⟨C$_6$H$_4$⟩SO$_2$CH$_3$ | 162–170° C (dec.) | 3480,3260,1770, 1670,1600,1545. | 235(14900), 283(7530), 378(36500). CH$_3$OH | 3.10s3H,3.80s2H,5.20d(5Hz)1H,5.73dd (8;5Hz)1H,6.83–7.90m7H,8.33s1H, 9.13d(8Hz)1H,11.20br1H. | −298° 0.288DMSO 25° C |
| 7 |  | =NNH—⟨C$_6$H$_4$⟩SO$_3$Na | 260° C (dec.) | 3380,3240,1763, 1665,1601,1540. | 236(15000), 273(9500), 367(28000). CH$_3$OH | 3.80s2H,5.15d(5Hz)1H,5.63dd(8;5Hz)1H, 6.85–7.65m7H,8.28s1H,9.07d(8Hz)1H, 12.33s1H. | −217.1° 0.562DMSO 24° C |
| 8 |  | =NNH—⟨pyridyl⟩ | 158–162° C (dec.) | 3180,3100,1782, 1655,1610,1541. | 236(15300), 352(17600). CH$_3$OH | 3.82s2H,4.00ABq(42;18Hz)2H,5.21d(5Hz) 1H,5.74dd(8;5Hz)1H,6.8–8.25m7H, 8.39s1H,9.17d(8Hz)1H. | −300° 0.4266DMSO 24.5° C |

-continued

| No. | Acyl | =Z | m.p. | IR-spectrum $\nu_{max}^{Nujol}$ cm$^{-1}$ | UV-spectrum $\nu_{max}^{EtOH}$ nm (ε) | NMR-spectrum $\delta^{s}6^{-DMSO}$ (60 MHz) | $[\alpha]_D^{t°C}(c)$ |
|---|---|---|---|---|---|---|---|
| 9 | ⌬-CH$_2$CO— (thiophene) | =NN⌬NCH$_3$ | 170–208° C (dec.) | 3280,1755,1675, 1645,1605,1545, 1520. | 233(11400), 364(37900). | — | — |
| 10 | ⌬-CH$_2$CO— | =NNH–⌬(N,S thiazole) | 178–183° C (dec.) | 3270,1792,1660, 1603,1543. | 225(23000), 355(23900). CH$_3$OH | 3.80s2H,5.23d(4.5Hz)1H,5.79dd(8;4.5Hz)1H, 6.8–7.2m5H,8.37s1H,9.15d(8Hz)1H. | −103.7° 0.3075DMSO 24° C |
| 11 | ⌬-CH$_2$CO— | =NNH–⌬ (SH·H$_2$O, NH$_2$ triazole) | 220–235° C (dec.) | 3260,1780,1717, 1667,1640,1550, 1495. | 240(16700), 262(15800), 336(20800). | 3.58s2H,5.20d(5Hz)1H,5.57dd(8;5Hz)1H, 6.8–7.5m3H,8.50s1H,9.17d(8Hz)1H,11.03 s1H. | −205° 0.308DMSO 25° C |
| 12 | ⌬-CH$_2$CO— | =NNH–⌬ (purine ring) | 210–215° C (dec.) | 3240,1770,1658, 1660,1595,1535. | — | — | — |
| 13 | ⌬-CH$_2$CO— | =NNH–⌬–SO$_2$ | 140–150° C (dec.) | 3500,3280,1790, 1660,1605,1530. | 228(15300), 317(7600), 400(37000). | 3.0–4.4(8H),3.83s2H,5.20d(5Hz)1H,5.97m2H, 6.77–7.6m,8.00s1H,9.13d(8Hz)1H. | +107° 0.303DMSO 25° C |
| 14 | ⌬-CH$_2$CO— | =NNHCH$_2$COOC$_2$H$_5$ | 126–135° C | 3270,1795,1745, 1665,1605,1540. | 345(12000). | — | — |
| 15 | ⌬-CH$_2$CO— | =NNHCHO H$_2$O | 150–160° C (dec.) | 3260,1780,1680, 1655,1535. | 232(14300), 313(24300). | — | — |
| 16 | ⌬-CH$_2$CO— | =NNHCOCH$_3$ H$_2$O | 184–190° C (dec.) | 3480,3255,1778, 1670,1648,1540. | 233.5(13800), 315(69300). | 1.95s+2.13s3H,3.85ABq(3 5;18Hz)2H,5.18d (5Hz)1H,5.76dd(8;5Hz)1H,6.8–7.5m3H, 8.18s+8.32s1H,9.13d(8.5Hz)1H. | −116.9° 0.4109CH$_3$OH 24.5° C |
| 17 | ⌬-CH$_2$CO— | =NNHCO—CH$_2$NH$_2$ | 204–209° C (dec.) | 3260,1767,1660, 1600,1585. | 235, 316. (saturated solution) | 3.58s2H,3.9dd2H,5.17d(2Hz)1H,5.75dd(8;4 Hz)1H,6.8–7.5m3H,9.20s1H,9.13d(8Hz)1H. | — |
| 18 | ⌬-CH$_2$CO— | =NNHCCH$_2$NH‖O·COOC$_4$H$_9$ | 210–215° C (dec.) | 3260,1775,1675, 1530. | 234(14000), 319(23900). | 1.40s9H,3.83s2H,5.18d(5Hz)1H,5.75dd(8;5 5Hz)1H,6.87–7.60m3H,8.20s+8.40s1H,9.12 d(8Hz)1H,11.42brH. | — |

| No. | Acyl | =Z | m.p. | IR-spectrum $\nu_{max}^{Nujol}$ cm$^{-1}$ | UV-spectrum $\nu_{max}^{EtOH}$ nm ($\epsilon$) | NMR-spectrum $\delta^{d_6-DMSO}$ (60 MHz) | $[\alpha]_D^t{}^\circ (c)$ |
|---|---|---|---|---|---|---|---|
| 19 | ⟨S⟩—CH$_2$CO— | =NNHCCH$_2$N(CH$_3$)$_3$ $\cdot$ Cl$^-$ ‖O | 196–206° C (dec.) | 3200,1785,1680, 1601,1533,1463. | 235(11800), 322(17800). | — | −109.0° 0.321DMSO 24.5° C |
| 20 | ⟨S⟩—CH$_2$CO— | =NNHCCH$_2$—N$^+$⟨py⟩ Cl$^-$ ‖O | 190–195° C (dec.) | 3160,1777,1692, 1633,1599,1533. | 233(15900), 319(21300). | 3.7–4.1m4H,5.27d(4Hz)1H,5.8–6.2m3H, 6.8–7.5m3H,8.0–9.3m7H,12.2br-s1H. | −69.7° 0.294H$_2$O 25° C |
| 21 | ⟨S⟩—CH$_2$CO— | =NNHCOCOOH | 173–176° C (dec.) | 3260,1779,1662 1598,1533. | 235(12300), 330(20000). | 3.77s2H,5.18d(5Hz)1H,5.75dd(8;5Hz)1H, 6.75–7.50m3H,8.60s1H,9.12d(8Hz)1H. | −176.5° 0.298DMSO 26° C |
| 22 | ⟨S⟩—CH$_2$CO— | =NNHCOCOOC$_2$H$_5$ $\cdot$ H$_2$O | 134–137° C (dec.) | 3260,1785,1690, 1600,1535. | 236(12100), 329(21200). | 1.28t(7Hz)3H,3.77s2H,4.28quintet(7Hz)2H, 5.22d(5Hz)1H,6.60dd(8;5Hz)1H,6.85–7.45m 3H,8.63s1H,9.12d(8Hz)1H,13.9Ss1H. | −155.6° 0.356CH$_3$OH 24.5° C |
| 23 | ⟨S⟩—CH$_2$CO— | =NNHCOCO—NH$_2$ | 190–195° C (dec.) | 3450,3270,1773 1674,1596. | 232(11500), 331(21600). | 3.79s2H,5.22d(5Hz)1H,5.79dd(8;5Hz)1H, 6.9–7.5m3H,8.0ld(9.5Hz)2H,8.70s1H, 9.18d(8Hz)1H,13.87s1H. | −228.9° 0.3421CH$_3$OH 24.5° C |
| 24 | ⟨S⟩—CH$_2$CO— | =NNHCOCONHNH$_2$ | 205–209° C (dec.) | 3480,3260,1783, 1660,1598. | 236; 341 (saturated solution) | 3.80s2H,5.22d(5Hz)1H,5.78dd(8;5Hz)1H, 6.85–7.45m3H,8.72s1H,9.17d(8Hz)1H. | −246.0° 0.4248DMSO 24.5° C |
| 25 | ⟨S⟩—CH$_2$CO— | =NNHCOCCH$_2$CN $\cdot$ H$_2$O ‖O | 143–150° C (dec.) | 3270,2260,1783, 1692,1602,1532. | 234(12400), 316(29100). | 3.80s2H,3.83ABq(49;18Hz)2H,4.12s2H, 5.20d(5Hz)1H,5.75dd(8;5Hz)1H,6.9–7.4m 3H,8.20s1H,9.13d(8Hz)1H,13.47s1H. | −107.2° 0.3150CH$_3$OH 24.5° C |
| 26 | ⟨S⟩—CH$_2$CO— | =NNHC(CHOH)$_4$CH$_2$OH ‖O | 132–138° C (dec.) | 3400,3300,1780, 1667,1605,1531. | 234(11300), 319(15800), 404(2700). | 3.52s2H,3.78s2H,5.20d(5Hz)1H,5.77dd (8;5Hz)1H,6.85–7.50m3H,8.48s1H, 9.13d(5Hz)1H. | −125.4° 0.427ODMSO 24.5° C |
| 27 | ⟨S⟩—CH$_2$CO— | =NNHCO—⟨C$_6$H$_4$⟩—H$_2$O | 170–180° C (dec.) | 3265,1785,1664, 1603,1541. | 234(19200), 330(27800). | 3.78s2H,5.22d(5Hz)1H,5.79dd(8.5;5Hz)1H, 6.8–8.1m9H,8.44s1H,9.15d(8.5Hz)1H, 10.19s1H. | −139° 0.417DMSO |
| 28 | ⟨S⟩—CH$_2$CO— | =NNHCO—⟨pyridyl⟩ N $\cdot$ H$_2$O | 193–198° C (dec.) | 3283,1779,1695, 1652,1639,1592, 1531,1504. | 334(66200). | 3.78s2H,5.23d(5Hz)1H,5.79dd(8;5Hz)1H, 6.8–7.m3H,7.6–8.0m2H,8.64s1H,8.4–8.9 m2H,9.16d(8Hz)1H,10.21s1H. | −139° 0.407 |
| 29 | ⟨S⟩—CH$_2$CO— | =NNHCO—⟨furyl⟩ | 160–168° C (dec.) | 3270,1795,1775, 1700,1665,1615, 1600,1540. | 240(13560), 336(30510). | 3.80s2H,5.23d(4Hz)1H,5.80dd(8;4Hz)1H, 6.63–8.03m6H,8.50s1H,11.70br-s1H. | −134° 0.303DMSO 25° C |

-continued

| No. | Acyl | =Z | m.p. | IR-spectrum $\nu_{max}^{Nujol}$ cm$^{-1}$ | UV-spectrum $\nu_{max}^{EtOH}$ nm ($\epsilon$) | NMR-spectrum $\delta_6$-DMSO (60 MHz) | $[\alpha]_D^C$(c) |
|---|---|---|---|---|---|---|---|
| 30 | thienyl-CH$_2$CO— | =NNHCO (isoxazole) | 160–195° C (dec.) | 3275,1795,1708, 1663,1602,1530. | 235(15300), 330(24900). | 3.37–4.37-2H,3.80sH,5.23d(5Hz)1H,5.80dd (8;5Hz)1H,6.70–7.47m4H,8.63s1H,8.77s1H, 9.13d(8Hz)1H. | — |
| 31 | thienyl-CH$_2$CO— | =NNHCO (methylisoxazole) | 150–160° C (dec.) | 3425,3260,3205, 1785,1723,1660, 1595,1530. | 236(15400), 330(22000). | 2.48s3H,3.80s2H,3.90ABq(32;18Hz)2H, 5.20d(5Hz)1H,5.77dd(8;5Hz)1H,6.63s1H, 6.80–7.50m3H,8.56s1H,9.20d(8Hz)1H. | — |
| 32 | thienyl-CH$_2$CO— | =NNHCO (thiadiazole-NH$_2$·½H$_2$O) | 148–153° C (dec.) | 3460,3210,1780, 1665,1596,1540, 1516. | 240(15200), 335(24000). | 3.80s2H,3.95ABq(37;17Hz)2H,5.25d(5Hz)1H, 5.80dd(8;5Hz)1H,6.9–7.5m3H,8.73s1H, 9.17d(8Hz)1H,9.27s1H,14.12s1H. | −144° 0.322DMSO 24° C |
| 33 | thienyl-CH$_2$CO— | =NNHCO (methylthiadiazole-NH$_2$) | 195–198° C (dec.) | 3290,3205,1789, 1711,1692,1665, 1590,1532. | 234(16200), 333(28800). | 2.88s3H,3.80s2H,3.93ABq(37;18Hz)2H, 5.23d(5Hz)1H,5.80dd(8;5Hz)1H,6.85–7.50m 3H,8.73s1H,9.17d(8Hz)1H,14.20s1H. | −176.4° 0.300DMSO 24° C |
| 34 | thienyl-CH$_2$CO— | =NN (pyridone·H$_2$O) | 197–200° C (dec.) | 3250,1780,1708, 1662,1641,1590, 1538. | 231(16800), 302(13800), 346(10770). | — | — |
| 35 | thienyl-CH$_2$CO— | =NNHSO$_2$-C$_6$H$_4$-CH$_3$ | 145–148° C (dec.) | 3200,1784,1662, 1596. | 227.5(20300), 311(1810). CH$_3$OH | 2.40s3H,4.14s2H,4.91d(5Hz)1H,5.81d (5Hz)1H,6.8–7.9m7H,8.13s1H. (CDCl$_3$ + CD$_3$OD) | −103.7° 0.355CH$_3$OH 23° C |
| 36 | thienyl-CH$_2$CO— | =NNHCOOCH$_3$ | 190–198° C (dec.) | 3520,3250,3205, 1788,1715,1665, 1593,1545,1503. | 233(14900), 313(26900). | 3.68s3H,3.78s2H,3.82ABq(32;18Hz)2H,5.18d (5Hz)1H,5.75dd(8;5Hz)1H,6.78–7.58m3H, 8.23s1H,9.13d(8Hz)1H,11.61s1H. | −95.5° 1.0105CH$_3$OH 24° C |
| 37 | thienyl-CH$_2$CO— | =NNHCOOC$_4$H$_9$-t | 155–180° C (dec.) | 3390,3270,1784, 1705,1600,1508. | 233(13700), 315(22800). | 1.45s9H,3.78s2H,3.80ABq(32;18Hz)2H,5.17d (5Hz)1H,5.72dd(8;5Hz)1H,6.8–7.5m3H,8.21s 1H,9.15d(8Hz)1H,10.97sH. | −150.2° 0.9929CHCl$_3$ 24° C |
| 38 | thienyl-CH$_2$CO— | =NNHCSCH$_3$, H$_2$O (C=S) | 168–179° C (dec.) | 3440,3250,3200, 1790,1687,1590, 1546,1500. | 233(12400), 291(7029), 357(38300). | 2.50s3H,3.78s2H,5.20d(5Hz)1H,5.75dd(8;5 Hz)1H,6.78–7.5m3H,8.43s1H,9.13d(8Hz)1H. | −261° 0.336DMSO 21.5° C |
| 39 | thienyl-CH$_2$CO— | =N-NH-C (oxo-imidazoline) | 184–190° C (dec.) | — | — | — | — |

What we claim is:
1. A compound of the following formula:

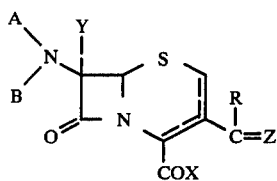

wherein A is hydrogen;
B is thienylacetyl;
R is hydrogen;
X is hydroxy;
Y is hydrogen or methoxy; and
Z is a hydrazino moiety selected from the group consisting of:
(1) hydrazono;
(2) 2-(o- or p-carboxyphenyl)hydrazono, 2-(p-alkylsulfonylphenyl)hydrazono in which said alkyl contains 1 to 3 carbon atoms, 2-(p-sulfophenyl)hydrazono which can form a slat with an alkali metal ion;
(3) 2-phenyl-2-alkylhydrazono in which the alkyl contains 1 to 3 carbon atoms;
(4) 2-(2-pyridyl)hydrazono, 2-(thiazol-2-yl)hydrazono, 2-(1-amino-5-mercapto-1,3,5-triazol-2-yl)hydrazono, 2-(purin-6-yl)-hydrazono, 2-(4-oxoimidazolin-2-yl)hydrazono;
(5) 2-(sulfolan-3-yl)hydrazono, 2-(carbalkoxymethyl)hydrazono in which the carbalkoxy contains 2 to 5 carbon atoms;
(6) (4-methylpyrazin-1-yl)imino, (2-pyridon-1-yl)imino;
(7) 2-(alkanoyl)hydrazono in which the alkanoyl contains 1 to 4 carbon atoms, 2-glycylhydrazono, 2-(n-tertiary butoxycarbonyl-glycyl)-hydrazono, 2-(trimethylammoniumacetyl)hydrazono, 2-(pyridiniumacetyl)hydrazono, 2-oxalylhydrazono, 2-(alkoxalyl)hydrazono in which the alkoxalyl contains 3 to 6 carbon atoms, 2-(amidoxalyl)hydrazono, 2-(hydrazinyldicarbonyl)hydrazono, 2-(cyanoacetyl)hydrazone, 2-(gluconoyl)hydrazono, 2-(benzoyl)hydrazono, 2-(furoyl)hydrazono, 2-(isoxazol-3-yl)carbonylhydrazono, 2-(5-methyl-isoxazol-3-yl)carbonylhydrazono, 2-(1,2,5-thiadiazol-3-yl)-carbonylhydrazono, 2-(5-methyl-1,2,3-thiadiazol-4-yl)carbonylhydrazono;
(8) 2-(carbalkoxy)hydrazono in which the carbalkoxy contains 2 to 5 carbon atoms, 2-(dithiocarbalkoxy)hydrazono in which the diethiocarbalkoxy contains 2 to 5 carbon atoms, 2-(methylthiothiocarbonyl) hydrazono and 2-(4-hydroxyimidazol-2-yl)hydrazono; and wherein the broken line shows the presence of a double bond at the 3-position, or an alkali metal salt thereof.
2. A compound selected from the group consisting of:
(1) 3-(2-p-carboxyphenylhydrazono)methyl-(2-thienylacetamido)-7-methoxy-3-cephem-4-carboxylic acid,
(2) 3-(2-acetylhydrazono)methyl-7-(2-thienylacetamido)-7-methoxy-3-cephem-4-carboxylic acid,
(3) 7-(2-thienylacetamido)-3-(2-ethoxalylhydrazono)-methyl-3-cephem-4carboxylic acid,
(4) 7-(2-thienylacetamido)-3-(2-acetylhydrazono)-methyl-3-cephem-4-carboxylic acid,
(5) 7-(2-thienylacetamido)-3-(2-formylhydrazono)-methyl-3-cephem-4-carboxylic acid,
(6) 7-(2-thienylacetamido)-3-(2-carbethoxymethylhydrazono)methyl-3-cephem-4-carboxylic acid,
(7) 3-(sulfolan-3-ylhydrazono)methyl-7-(2-thienylacetamido)-3-cephem-4-carboxylic acid,
(8) 3-(2-acetylhydrazono)methyl-7-(2-thienylacetamido)-3-cephem-4-carboxylic acid,
(9) 3-hydrazonomethyl-7-(2-thienylacetamido)-3-cephem-4-carboxylic acid and
(10) 3-(2-glycylhydrazono)methyl-7-(2-thienylacetamido)-3-cephem-4-carboxylic acid.
3. The compound 3-(2-acetylhydrazono)methyl-7-(2-thienylacetamido)-7-methoxy-3-cephem-4-carboxylic acid.
4. An antibacterial pharmaceutical composition comprising an effective antibacterial amount of the compond of claim 1, and a pharmaceutically acceptable carrier.
5. An antibacterial pharamaceutical composition for parenteral administration comprising from 0.1 to 10 grams of the compound of claim 1 in the form of a powder, lyophilizate or crystals in a vial.
6. A compound according to claim 1, wherein A, Y and R are each hydrogen; B is thienylacetyl; X is hydroxy; the broken line designates a double bond at the 3-position; and Z is a moiety selected from the group consisting of: hydrzono, 2-methyl-2-phenylhydrazono, 2-(o- or p-carboxyphenyl)hydrazono, 2-p-methanesulfonylphenyl)-hydrazono, 2-(sodiooxysulfonylphenyl)-hydrazono, 2-(2-pyridyl)-hydrazono, 2-(N'-methyl-1,4-dihydropyrazin-1-yl)imino, 2-(thiazol-2-yl)hydrazono, 2-(5-mercapto-1-amino-1,3,4-triazol-2-yl)hydrazono, 2-(purin-6-yl)hydrazono, 2-(sulfolan-3-yl)hydrazono), 2-(carbethoxymethyl)hydrazono, 2-(carbomethoxymethyl)hydrazono, 2-formylhydrazono, 2-acetylhydrazono, 2-glycylhydrazono, 2-(N-tertiary butoxycarbonylglycyl)hydrazono, 2-trimethylammoniumacetyl)-hydrazono, 2-(pyridiniumacetyl)hydrazono, 2-oxalylhydrazono, 2-ethoxalylhydrazono, 2-amidoxalylhydrazono, 2-(hydrazinyldicarbonyl)-hydrazono, 2-cyanoacetyl)hydrazono, 2-gluconoylhydrazono, 2-benzoyl-hydrazono, 2-furoylhydrazono, 2-(isoxazol-3-yl)carbonylhydrazono, 2-(5-methylisoxazol-3-yl)carbonylhydrazono, 2-(1,2,5-thiadiazol-4-yl)carbonylhydrazono, 2-(5-methyl-1,2,3-thiadiazol-4-yl)carbonylhydrazono, (2-pyridon-1-yl)imino, 2-carbomethoxyhydrazono, 2-(tertiary butoxycarbonyl)hydrazono, 2-(methylthiothiocarbonyl)-hydrazono, and 2-(4-hydroxyimidazol-2-yl)hydrazono, and alkali metal salts thereof.
7. A compound according to claim 1, wherein A and R are each hydrogen; Y is methoxy; B is thienylacetyl; X is hydroxy; and Z is acetylhydrazono or 2-(p-carboxyphenyl)hydrazono; and wherein the broken line designates a double bond at the 3-position, and alkali metal salts thereof.

* * * * *